US010610558B2

(12) United States Patent
Hiraishi et al.

(10) Patent No.: US 10,610,558 B2
(45) Date of Patent: Apr. 7, 2020

(54) PROPHYLACTIC AND/OR THERAPEUTIC AGENT FOR NAFLD/NASH

(71) Applicants: ADABIO CO., LTD., Gunma (JP); OTSUKA PHARMACEUTICAL FACTORY, INC., Tokushima (JP)

(72) Inventors: Katsuya Hiraishi, Gunma (JP); Fumie Jimma, Gunma (JP); Hiroyuki Soma, Gunma (JP); Taro Adachi, Gunma (JP); Masakazu Adachi, Gunma (JP); Ippei Yamaoka, Tokushima (JP); Tomohiro Kagawa, Tokushima (JP)

(73) Assignees: ADABIO CO., LTD., Gunma (JP); OTSUKA PHARMACEUTICAL FACTORY, INC., Tokushima (JP)

( * ) Notice: Subject to any disclaimer, the term of this patent is extended or adjusted under 35 U.S.C. 154(b) by 85 days.

(21) Appl. No.: 15/776,108

(22) PCT Filed: Nov. 25, 2016

(86) PCT No.: PCT/JP2016/004963
§ 371 (c)(1),
(2) Date: May 15, 2018

(87) PCT Pub. No.: WO2017/090253
PCT Pub. Date: Jun. 1, 2017

(65) Prior Publication Data
US 2018/0325975 A1 Nov. 15, 2018

(30) Foreign Application Priority Data
Nov. 27, 2015 (JP) .................................. 2015-232053

(51) Int. Cl.
*A61K 36/736* (2006.01)
*A23L 33/105* (2016.01)
(Continued)

(52) U.S. Cl.
CPC ............ *A61K 36/736* (2013.01); *A23L 2/385* (2013.01); *A23L 33/105* (2016.08); *A61P 1/16* (2018.01); *A23V 2002/00* (2013.01)

(58) Field of Classification Search
CPC ..................................................... A61K 36/736
See application file for complete search history.

(56) References Cited

U.S. PATENT DOCUMENTS

| 2006/0140974 A1* | 6/2006 | Choe ...................... A61K 36/06 424/195.16 |
| 2016/0031763 A1* | 2/2016 | Kim ......................... C05D 1/00 504/101 |
| 2016/0263130 A1 | 9/2016 | Lee et al. |

FOREIGN PATENT DOCUMENTS

| JP | 2003-265138 A | 9/2003 |
| JP | 2007-143452 A | 6/2007 |
| JP | 2011-201841 A | 10/2011 |

OTHER PUBLICATIONS

Kajal Dhabalia, Ume: helper of many things, Wholesome Soul, https://blog.wholesomesoul.com/ume-helper-of-many-things/, 2013.*

(Continued)

*Primary Examiner* — Rosanne Kosson
(74) *Attorney, Agent, or Firm* — Greenblum & Bernstein, P.L.C.

(57) ABSTRACT

The present invention provides a prophylactic and/or therapeutic agent for non-alcoholic fatty liver disease (NAFLD), and particularly non-alcoholic steatohepatitis (NASH) comprising an ume (Japanese apricot) juice concentrate or a processed product thereof. The prophylactic and/or therapeutic agent is obtained by utilizing a component contained in a plant or a processed product thereof, and hence is safe and easily taken. It has been confirmed that when the ume juice concentrate or the processed product thereof is orally administered to a streptozocin (STZ)-induced NAFLD (Continued)

MOUSE TO WHICH NEUTRALIZED DILUTED UME JUICE CONCENTRATE WAS ADMINISTERED model mouse or an STZ-induced NASH model mouse, liver fibrogenesis can be reduced.

9 Claims, 9 Drawing Sheets

(51) Int. Cl.
*A61P 1/16* (2006.01)
*A23L 2/385* (2006.01)

(56) References Cited

OTHER PUBLICATIONS

Stål, "Liver Fibrosis in Non-Alcoholic Fatty Liver Disease—Diagnostic Challenge with Prognostic Significance" *World Journal of Gastroenterology*, vol. 21, No. 39, pp. 11077-11087, 2015.
Bian et al., "Liver Fibrogenesis in Non-Alcoholic Steatohepatitis" *Frontiers in Physiology*, vol. 3, art. 248, pp. 1-7, 2012.
Ken'ichi Ikeshima et al., "Topics update in NAFLD: from bench side to clinics", Japanese Journal of Gastroenterology, vol. 111, No. 1, pp. 4-13, Jan. 2014.
Akihiro Matsumoto, "Hi Alcohol-sei Shibo-sei Kan Shikkan (NAFLD)", Medical Journal of Aizawa Hospital, vol. 12, pp. 1-4, 2014.
Masakazu Takahashi et al., "Suppressive Effect on Lipid Accumulation in Hepatocytes by Prunus mume Extracts and Edible Oil Constituent of Perilla frutescens var. Frutescens Cultivates in Fukui", Journal of Fukui Prefectural University, No. 45, pp. 47-55, Aug. 2015.
Hokari et al., "Efficacy of MK615 for the treatment of patients with liver disorders", World Journal of Gastroenterology, vol. 18(31), pp. 4118-4126, Aug. 21, 2012.
Haruhisa Nakao et al., "NASH (non-alcholic steatohepatitis)", Mebio, vol. 26, No. 11, pp. 82-89, Nov. 2009.
International Search Report issued with respect to Patent Application No. PCT/JP2016/004963, dated Dec. 27, 2016.
International Preliminary Report on Patentability issued with respect to Patent Application No. PCT/JP2016/004963, dated May 29, 2018.

\* cited by examiner

FIG. 1A  STANDARD MOUSE

FIG. 1B  CONTROL MOUSE

FIG. 1C  MOUSE TO WHICH NEUTRALIZED DILUTED UME JUICE CONCENTRATE WAS ADMINISTERED

FIG. 6A    CONTROL MOUSE

FIG. 6B    MOUSE TO WHICH NEUTRALIZED DILUTED UME JUICE CONCENTRATE WAS ADMINISTERED

CONTROL

FIG. 9B

MOUSE TO WHICH NEUTRALIZED
DILUTED UME JUICE CONCENTRATE
WAS ADMINISTERED

FIG. 10A  CONTROL RAT: HEMATOXYLIN/EOSIN STAINING (MAGNIFICATION: 400)

FIG. 10B  RAT TO WHICH DILUTED UME JUICE CONCENTRATE WAS ADMINISTERED: HEMATOXYLIN/EOSIN STAINING (MAGNIFICATION: 400)

FIG. 10C  CONTROL RAT: ANTI-α SMOOTH MUSCLE ACTIN IMMUNOSTAINING (MAGNIFICATION: 1000)

PROPHYLACTIC AND/OR THERAPEUTIC AGENT FOR NAFLD/NASH

TECHNICAL FIELD

The present invention relates to a prophylactic and/or therapeutic agent for non-alcoholic fatty liver diseases (NAFLD), and particularly non-alcoholic steatohepatitis (NASH), containing an ume (Japanese apricot) juice concentrate or a processed product thereof, and a method for preparing the prophylactic and/or therapeutic agent.

BACKGROUND ART

The liver is the largest organ having a variety of functions over 500 functions, and works not only to reprocess various nutrients having been absorbed by intestines to supply the resultants to the other organs and store an excessive portion but also to make a large number of actions necessary for sustaining life, such as generation and secretion of bile, detoxification and excretion. This organ is, however, easily disturbed by various factors such as irregular life, stress, viruses, drugs, alcohols, undernourishment and hepatic circulatory system disorder, which may lead to a disease such as acute hepatitis, chronic hepatitis, fatty liver or liver cirrhosis in some cases. In Japan in particular, it is said that 15% or more of adults (estimated as 1.5 to 2 million persons) have fatty liver, and the spread to the young generation has become a serious social problem.

It was regarded that fatty liver is a pathological condition relating mainly to alcoholic liver disease caused by drinking an excessive amount of alcohol. Alcoholic fatty liver refers to a pathological condition in which fat is accumulated in the liver of alcohol drinkers to form fat droplets in liver cells, and fat (neutral fat in particular) is further deposited in the liver cell to cause the liver damage. In recent years, however, it has been found that findings similar to alcoholic liver disease occur even in non-drinkers.

An example of the pathological condition of fatty liver disease occurring in non-drinkers includes non-alcoholic fatty liver disease (NAFLD). NAFLD is such simple fatty liver that about 90% of patients of the disease can improve the symptom by proper diet therapy or exercise therapy although fatty liver including deposition of neutral fat in liver cells is found.

It is known, however, that about 10% of cases of NAFLD is non-alcohol steatohepatitis (NASH) corresponding to a progressive pathological condition. Although medical consensus on histopathological progression of NASH has not been obtained yet, it is regarded that a certain consensus has been built that liver cells having fat accumulated therein are modified or necrosed to cause steatohepatitis having inflammatory findings or fibrogenesis in liver tissue. Besides, it is said that a probability that fatty liver progresses to NASH, and further to more serious liver fibrosis, liver cirrhosis or liver cancer is higher in a subject suffering from multiple risk factors such as metabolic syndrome, obesity, diabetes, hyperlipidemia, hypertension and hyperuricemia.

On the other hand, ume (the flesh of ume) has been known from old days as home remedy for fatigue recovery, food poisoning and the like, and a food for inducing autophagy containing a neutralized product of ume extract (ume flesh extract) (see, for example, patent document 1), a liver function improving agent for a patient of viral hepatitis containing a neutralized product of ume extract (see, for example, patent document 2) and the like have been proposed. Besides, it has been reported that ume extract obtained by concentrating, 20 times by heating, an ume squeezed liquid prepared by squeezing ume, neutralizing the resultant with NaOH, and sterilizing the resultant by heating is effective for galactosamine hydrochloride-induced acute liver injury rat (for example, see non-patent document 1).

PRIOR ART DOCUMENTS

Patent Documents

Patent Document 1: Japanese unexamined Patent Application Publication No. 2007-143452
Patent Document 2: Japanese unexamined Patent Application Publication No. 2011-201841

Non-Patent Documents

Non-patent Document 1: World Gastroenterol. 2012, Vol. 18 (31) 4118-4126

SUMMARY OF THE INVENTION

Object to be Solved by the Invention

An object of the present invention is to provide a prophylactic and/or therapeutic agent for NAFLD, and particularly NASH, which is obtained by utilizing a component contained in a plant or a processed product thereof, is safe and easily taken, and is used for preventing and/or treating NAFLD, and particularly NASH.

Means to Solve the Object

The present inventors have searched, in components that are safe, easily taken and contained in natural products such as plants, for a component improving NAFLD, and particularly NASH, and have found that when an ume juice concentrate or a processed product thereof known to have an effect against viral hepatitis mainly caused by infection with virus or acute hepatitis caused by administration of a poisonous material or the like is administered to a streptozocin (STZ)-induced NASLD model mouse or an STZ-induced NASH model mouse, liver fibrogenesis, that is, one of pathological conditions of NAFLD, and particularly of NASH can be reduced, resulting in accomplishing the present invention.

Specifically, the present invention provides the following:
(1) A prophylactic and/or therapeutic agent for non-alcoholic fatty liver disease (NAFLD), comprising an ume juice concentrate or a processed product thereof.
(2) The prophylactic and/or therapeutic agent according to (1) described above, wherein the processed product of the concentrate is a neutralized processed product of the concentrate.
(3) The prophylactic and/or therapeutic agent according to (1) or (2) described above, wherein the concentrate is a heated concentrate.
(4) The prophylactic and/or therapeutic agent according to any one of (1) to (3) described above, which is for oral administration.
(5) The prophylactic and/or therapeutic agent according to any one of (1) to (4) described above, which is used as a dietary-supplement.
(6) The prophylactic and/or therapeutic agent according to any one of (1) to (5) described above, which reduces fibrogenesis in liver tissue.

(7) The prophylactic and/or therapeutic agent according to any one of (1) to (6) described above, wherein the non-alcoholic fatty liver disease (NAFLD) is non-alcoholic steatohepatitis (NASH).

(8) A method for preparing a prophylactic and/or therapeutic agent for non-alcoholic fatty liver disease (NAFLD), comprising the following steps (a) and (b):

(a) preparing an ume squeezed liquid from green ume; and (b) preparing an ume juice concentrate by concentrating the ume squeezed liquid prepared in the step (a).

(9) The method for preparing a prophylactic and/or therapeutic agent according to (8) described above, wherein the concentration performed in the step (b) is concentration by heating.

(10) The method for preparing a prophylactic and/or therapeutic agent according to (8) or (9) described above, further comprising the following step (c):

(c) preparing a neutralized ume juice concentrate or a heated neutralized ume juice concentrate by neutralizing the ume juice concentrate or the heated ume juice concentrate prepared in the step (b).

(11) The method for preparing a prophylactic and/or therapeutic agent according to any one of (8) to (10) described above, wherein the non-alcoholic fatty liver disease (NAFLD) is non-alcoholic steatohepatitis (NASH).

(12) A food product comprising an ume juice concentrate or a processed product thereof.

(13) The food product according to (12) described above, wherein the processed product of the concentrate is a neutralized product of the concentrate.

(14) The food product according to (12) or (13) described above, wherein the concentrate is a heated concentrate.

(15) The food product according to any one of (12) to (14) described above, wherein the food product is a food for the sick, a food product for specified health uses or a food product with function claims.

(16) A food additive comprising an ume juice concentrate or a processed product thereof as an active ingredient.

(17) The food additive according to (16) described above, wherein the processed product of the concentrate is a neutralized processed product of the concentrate.

(18) The food additive according to (16) or (17) described above, wherein the concentrate is a heated concentrate.

(19) The food additive according to any one of (16) to (18) described above, for use in the production of a food product for the sick, a food product for specified health uses or a food product with function claims.

(20) An ume juice concentrate or a processed product thereof for use in preventing and/or treating non-alcoholic fatty liver disease (NAFLD).

(21) The ume juice concentrate or the processed product thereof according to (20) described above, wherein the processed product of the concentrate is a neutralized processed product of the concentrate.

(22) The ume juice concentrate or the processed product thereof according to (20) or (21) described above, wherein the concentrate is a heated concentrate.

(23) The ume juice concentrate or the processed product thereof according to any one of (20) to (22) described above, for oral administration.

(24) The ume juice concentrate or the processed product thereof according to any one of (20) to (23) described above, which is used as a dietary-supplement.

(25) The ume juice concentrate or the processed product thereof according to any one of (20) to (24) described above, which reduces fibrogenesis in liver tissue.

(26) The ume juice concentrate or the processed product thereof according to any one of (20) to (25) described above, wherein the non-alcoholic fatty liver disease (NAFLD) is non-alcoholic steatohepatitis (NASH).

(27) A prophylactic and/or therapeutic method for non-alcoholic fatty liver disease (NAFLD), comprising administering an effective amount of an ume juice concentrate or a processed product thereof to a subject.

(28) The method according to (27) described above, wherein the processed product of the concentrate is a neutralized processed product of the concentrate.

(29) The method according to (27) or (28) described above, wherein the concentrate is a heated concentrate.

(30) The method according to any one of (27) to (29) described above, the ume juice concentrate or the processed product thereof is for oral administration.

(31) The method according to any one of (27) to (30) described above, wherein the ume juice concentrate or the processed product thereof is used as a dietary-supplement.

(32) The method according to any one of (27) to (31) described above, which reduces fibrogenesis in liver tissue.

(33) The method according to any one of (27) to (32) described above, wherein the non-alcoholic fatty liver disease (NAFLD) is non-alcoholic steatohepatitis (NASH).

(34) A method for producing a prophylactic and/or therapeutic agent for non-alcoholic fatty liver disease (NAFLD) containing an effective amount of an ume juice concentrate or a processed product thereof.

(35) The method according to (34) described above, wherein the processed product of the concentrate is a neutralized product of the concentrate.

(36) The method according to (34) or (35) described above, wherein the concentrate is a heated concentrate.

(37) The method according to any one of (34) to (36) described above, wherein the prophylactic and/or therapeutic agent is for oral administration.

(38) The method according to any one of (34) to (37) described above, wherein the prophylactic and/or therapeutic agent is used as a dietary-supplement.

(39) The method according to any one of (34) to (38) described above, wherein the prophylactic and/or therapeutic agent reduces fibrogenesis in liver tissue.

(40) The method according to any one of (34) to (39) described above, wherein the non-alcoholic fatty liver disease (NAFLD) is non-alcoholic steatohepatitis (NASH).

Effect of the Invention

According to the present invention, fibrogenesis of liver tissue of patients with NAFLD, and particularly of NASH is reduced so that NAFLD, and particularly NASH can be treated, and the incidence of NAFLD, and particularly NASH in non-drinkers is lowered so that NAFLD, and particularly NASH can be prevented.

BRIEF DESCRIPTION OF DRAWINGS

FIGS. 1A, 1B and 1C are diagrams illustrating liver tissue subjected to hematoxylin staining/Sirius red staining.

FIGS. 6A and 6B are diagrams illustrating liver tissue subjected to hematoxylin staining/Sirius red staining.

FIGS. 9A and 9B are diagrams illustrating liver tissue subjected to hematoxylin/eosin staining.

FIGS. 10A, 10B and 10C are micrographs, where

DETAILED DESCRIPTION OF THE INVENTION

A prophylactic and/or therapeutic agent for NAFLD, and particularly NASH of the present invention is not especially limited as long as it is a prophylactic agent and/or a therapeutic agent containing an ume juice concentrate or a processed product thereof, and is preferably for oral administration. A suitable example of the concentrate is a heated concentrate, and an example of the processed product of the concentrate includes a diluted and/or neutralized product of the concentrate (hereinafter, a neutralized product of the concentrate is sometimes referred to as the "neutralized ume juice concentrate"). The prophylactic and/or therapeutic agent for NAFLD or NASH of the present invention can be used in the form of a medicine or a dietary-supplement. Another aspect of the present invention provides an ume juice concentrate or a processed product thereof to be used for preventing and/or treating NAFLD, and particularly NASH, use of an ume juice concentrate or a processed product thereof in production of a prophylactic and/or therapeutic agent for NAFLD or NASH, and a prophylactic and/or therapeutic method for NAFLD, and particularly NASH including orally administering, to a subject, an ume juice concentrate or a processed product thereof.

Besides, a preparation method for a prophylactic and/or therapeutic agent for NAFLD, and particularly NASH of the present invention is not especially limited as long as it includes a step (a) of preparing an ume squeezed liquid from green ume; and a step (b) of preparing a (heated) ume juice concentrate by concentrating (by heating) the ume squeezed liquid prepared in the step (a), and a step (c) of preparing a (heated) neutralized ume juice concentrate by neutralizing the (heated) ume juice concentrate prepared in the step (b) is preferably included.

NASH of the present invention can be a pathological condition of inflammation accompanied by steatosis and inflammatory cell infiltration or a pathological condition of progression of fibrogenesis occurring in liver tissue of non-drinkers that is not infected with virus such as hepatitis C virus (HCV) or hepatitis B virus (HBV) and does not have obvious drinking history. The fibrogenesis of liver tissue refers to replacement of lost tissue through accumulation of fibroblasts including activated stellate cells or myofibroblasts, or accumulation of intercellular matrixes such as collagen generated by fibroblasts, which is caused by loss of hepatocytes or dysfunction of tissue through necrosis or damage of liver cells begun to show symptoms of steatosis or proinflammatory changes, and it is regarded that the fibrogenesis of liver tissue contributes to retention of a physical form but does not recover the function of the liver tissue. When excessive deposition of fibrous protein such as collagen and hardening of tissue accompanied by invasive increase of fibroblasts are found not locally but widely in liver tissue, the pathological condition further develops and progresses to more serious liver fibrosis or liver cirrhosis. NAFLD of the present invention can be a pathological condition in which neutral fat is deposited in liver cells in liver tissue of non-drinkers, and in addition to the pathological conditions of NASH described above, includes simple fatty liver and a pathological condition that does not meet the definition of NASH, obvious accumulation of inflammatory cells and obvious fibrogenesis, but can be regarded as transition process to NASH in which localized steatotic necrosis of liver parenchyma or interstitial expansion of centrilobular field or portal field is found. Besides, it is said that mild elevation (about double to four times of a healthy level) of ALT level or AST level in blood is found in a blood test in many cases, and that ALT in particular is significantly elevated in many cases.

An effect of the prophylactic and/or therapeutic agent for NAFLD, and particularly NASH of the present invention can be reduction of liver fibrogenesis in NASH patients, and a method for confirming whether or not the liver fibrogenesis or inflammation of liver tissue has been reduced can be a method in which confirmation is made in a liver tissue image prepared by staining a liver tissue section. Examples of a method for staining a liver tissue section include aniline blue staining, trichrome staining, silver impregnation, Azan-Mallory staining, hematoxylin/eosin staining, Sirius red staining and hematoxylin staining/Sirius red staining. Among these, the hematoxylin staining/Sirius red staining, in which fiber and related tissue thereof can be stained in an enhanced manner by causing, after staining nucleus and cytoplasm with a metal complex dye such as hematoxylin, hydrophilic and high molecular Sirius red to bond to the cationic metal complex dye, can be suitably employed.

A case where the liver fibrogenesis is reduced by the administration of the prophylactic and/or therapeutic agent for NAFLD, and particularly NASH of the present invention can be a case where fibrogenetic regions are found, through visual evaluation of the liver tissue image with a microscope or the like, to be reduced or eliminated after the administration, or a case where staining positive regions are found, through analysis with the staining positive region extracted using an application of image analyzer, to be reduced or eliminated after the administration. Incidentally, the improvement in the pathological condition of NASH of the present invention is attained by the reduction of the liver fibrogenesis, and may be accompanied by increase of a plasma albumin level or a plasma total protein level. Incidentally, the reduction of the liver fibrogenesis can involve, for convenience, recovery of liver tissue owing to the reduction of liver fibrosis having been started to be formed, and suppression of start of the liver fibrogenesis.

Examples of a subject (person) to be administered with the prophylactic and/or therapeutic agent for NAFLD, and particularly NASH of the present invention include a person that is diagnosed with NAFLD or NASH and needs to be treated for NAFLD or NASH; and a person that is not diagnosed with NAFLD or NASH but needs/desires to prevent NAFLD or NASH, for example, such a person regarded to have high possibility of developing NAFLD or NASH as is suffering from metabolic syndrome, obesity, diabetes, hyperlipidemia, hypertension, hyperuricemia, etc.

A dosage form of the prophylactic and/or therapeutic agent for NAFLD, and particularly NASH of the present invention can be appropriately set in accordance with the health condition, severity of symptoms, the age, and the weight of the subject to be administered, and determination made by a doctor, and a dosage form for oral administration is preferred. An example of an oral dose for a human is, in terms of a diluted solution of a neutralized ume juice concentrate (a 1.7-fold diluted solution of Example 3), 30 to 600 mg/kg/day, preferably 40 to 370 mg/kg/day, and more preferably 80 to 300 mg/kg/day.

In formulation of the prophylactic and/or therapeutic agent for NAFLD, and particularly NASH of the present invention, another optional component can be added if necessary. Examples of the optional component include pharmaceutically acceptable usual carriers such as crystalline cellulose, gelatin, lactose, starch, magnesium stearate, talc, vegetable and animal fats, oils and fats, gum and polyalkylene glycol, and various ingredients for formulation, such as a binder, a stabilizer, a solvent, a dispersion medium, an extending agent, an excipient, a diluent, a pH buffer, a disintegrating agent, a solubilizing agent, a dissolution assisting agent and an isotonic agent.

The step (a) in the preparation method for the prophylactic and/or therapeutic agent for NAFLD, and particularly NASH of the present invention can be a step of preparing an ume squeezed liquid from green ume, and can be a step of preparing an ume squeezed liquid in a ratio of preferably 0.2 to 0.6 with respect to 1 of green ume. A specific example includes a step of preparing an ume squeezed liquid by squeezing a roughly crushed flesh of green ume or a frozen and thawed flesh of green ume using any of various squeezers or a centrifugal separator, and collecting a resultant ume squeezed liquid. A method for obtaining the roughly crushed flesh of green ume can be a method in which green ume is crushed using a mixer or the like. As the green ume, green ume immediately after harvest is preferably used, or green ume immediately after harvest having been frozen and stored until immediately before the preparation of the ume squeezed liquid is preferred.

The step (b) in the preparation method for a prophylactic and/or therapeutic agent for NAFLD, and particularly NASH of the present invention can be a step of preparing an ume juice concentrate by concentrating the ume squeezed liquid prepared in the step (a), and preferably a heated ume juice concentrate by heating and concentrating it, and can be a step of preparing a (heated) ume juice concentrate in a ratio of preferably 0.07 to 0.2, more preferably 0.075 to 0.15, and further preferably 0.08 to 0.12 with respect to 1 of the ume squeezed liquid. A specific example includes a step of preparing a (heated) ume juice concentrate with a Brix value of 70 to 80% by concentrating the ume squeezed liquid under reduced pressure or by heating it with 100° C. or more kept for boiling.

The step (c) in the preparation method for a prophylactic and/or therapeutic agent for NAFLD, and particularly NASH of the present invention can be a step of preparing a (heated) neutralized ume juice concentrate by neutralizing the (heated) ume juice concentrate prepared in the step (b), and the (heated) ume juice concentrate is preferably diluted before the neutralization. For example, a diluted solution of the (heated) ume juice concentrate can be prepared by adding water or a proper solvent in a ratio of preferably 0.5 to 6.0, more preferably 0.75 to 4.3, and further preferably 1.0 to 2.0 with respect to 1 of the (heated) ume juice concentrate.

Subsequently, the diluted solution of the (heated) ume juice concentrate is neutralized. Specifically, a solution of a (heated) neutralized ume juice concentrate can be prepared by adding an alkaline solution to the diluted solution of the (heated) ume juice concentrate to adjust pH of the diluted solution of the (heated) ume juice concentrate to preferably pH 5.0 to 8.0, more preferably pH 5.4 to 7.2, and further preferably pH 6.5 to 7.0. Examples of the alkaline solution include a NaOH aqueous solution and a KOH aqueous solution.

Insolubles such as a non-dispersible solid and a non-flowable solid can be removed from the solution of the (heated) neutralized ume juice concentrate by using a filter or centrifugal separator. Alternatively, insolubles are removed from the solution of the (heated) neutralized ume juice concentrate by using a mesh, and the resultant can be diluted to obtain a product.

The (heated) neutralized ume juice concentrate of the present invention is usually obtained by diluting the (heated) ume juice concentrate in a prescribed dilution ratio. The prescribed dilution ratio is, for example, 1.5 to 20-fold, preferably 2 to 10-fold, and more preferably 3 to 5-fold.

The ume juice concentrate or the processed product thereof of the present invention can be used not only as a prophylactic and/or therapeutic agent for non-alcoholic fatty liver disease (NAFLD) but also in the field of food. Examples include various foods (such as general foods including what is called health foods, foods for special dietary uses, foods with health claims, food materials and drinks) and food additives each containing the ume juice concentrate or the processed product thereof of the present invention. The foods for special dietary uses include foods for the sick, foods for specified health uses, powdered milk for expectant and nursing mothers/lactating mothers, formulated powdered milk for infants and foods for persons with dysphagia. The foods with health claims include foods for specified health uses, foods with nutrient function claims and foods with function claims. The ume juice concentrate or the processed product thereof of the present invention can be particularly suitably used in production of a food for the sick, a food for specified health uses, a food with function claims and the like. The ume juice concentrate or the processed product thereof of the present invention can be ingested as food directly in the original form (of a paste) without adding any other substances. Alternatively, the ume juice concentrate or the processed product thereof of the present invention may be powdered or granulated by a usual method if necessary. Besides, after adding, to the ume juice concentrate or the processed product thereof of the present invention, an appropriate aid such as a rice powder, an oil or fat, a starch, lactose, maltose, a vegetable oil or fat powder, a cocoa butter powder or stearic acid, the resultant may be formed by a usual method into a form suitable for eating, such as a paste, a drink, a soft capsule, a seamless capsule, a hard capsule, a granule or a pill, or the resultant may be added, for use, to any of various foods such as bread including simple bread and sweet buns; jams; biscuits; cookies; sweets such as crackers; cakes; chewing gums; instant food such as instant noodles, instant miso soups and instant soups; ice creams; and drinks such as yogurt, milk, health drinks and refreshing drinks (including Japanese tea, coffee, tea and juices). In this case, a blending amount of the ume juice concentrate or the processed product thereof of the present invention is appropriately set in accordance with the type, the state and the like of the food composition.

The present invention will now be more specifically described with reference to Examples, and it is noted that the technical scope of the present invention is not limited to the following exemplified description.

Example 1

Preparation of Solution of Neutralized Ume Juice Concentrate

Twenty (20) kg of green ume immediately after harvest was crushed using a mixer, the thus roughly crushed ume flesh was squeezed with a squeezer utilizing centrifugal force, and the resultant squeezed liquid was collected to obtain 8 kg of an ume squeezed liquid. The ume squeezed liquid was concentrated over about 90 hours by keeping on heating and boiling, the resultant was subjected to a heat treatment by keeping a temperature of 100° C. or more for another 24 hours, and thus, 0.4 kg of a heated ume juice concentrate (Brix of 75%) was obtained.

The heated ume juice concentrate was diluted with water of a substantially equivalent weight to obtain a solution of the heated ume juice concentrate, the solution of the heated ume juice concentrate was neutralized to pH 6.8 by adding an 8N NaOH aqueous solution thereto, and the resultant was diluted with purified water to obtain a neutralized ume juice concentrate (37 w/v % solution). This solution of the neutralized ume juice concentrate was centrifuged at 3000 rpm to precipitate insolubles. The resultant was sterilized with a sterile filter (pore size of 0.2 μm, manufactured by Sartorius), and thus, a solution of the neutralized ume juice concentrate with insolubles removed was obtained.

Example 2

Preparation of STZ-Induced NASH Model Mouse

C57BL/6J mice were administered with streptozocin (STZ) to prepare STZ-induced NASH model mice. The outline was as follows.

Thirty (30) C57BL/6J mice (manufactured by Charles River Laboratories Japan, Inc.) pregnant for 17 days were individually raised by allowing them to freely eat, as a standard diet, gamma-ray irradiated solid feed (CRF-1, manufactured by Oriental Yeast Co., Ltd.) and to freely drink distilled water, and were allowed to give birth. The thus obtained newborn mice were divided, at a ratio of 4:1, into mice to be administered with STZ and mice not to be administered (standard mice).

Twenty (20) μL of a 10 mg/mL solution of STZ (manufactured by Sigma) (0.1 M citrate buffer pH 4.5) was subcutaneously administered to the back of each of the mice to be administered with STZ by using an insulin syringe (Myjector, manufactured by Terumo Corporation) on day 2 assuming that the day of birth was day 0. After the STZ administration, the mice were raised by breastfeeding until they became 4 weeks old. On a day when the mice became 4 weeks old and 4 weeks had elapsed after the STZ administration, distinction between male and female was performed to select male mice. On the same day, the male mice were fasted for 6 hours, and were measured for a blood glucose level in blood collected from a caudal vein using a simple glucose level measuring device (Glutest Neo, manufactured by Sanwa Kagaku Kenkyusho Co., Ltd.).

When 6 hours had elapsed after starting the fast, the mice were weaned, and thereafter were fed with a high-fat diet (HFD 32, manufactured by Clea Japan Inc.) to be continuously raised as a group of STZ-induced NASH model mice. The standard mice not administered with STZ were fed with CRF-1 instead of the high-fat diet.

Example 3

Administration of Neutralized Ume Juice Concentrate

Mice Grouping

In the group of STZ-induced NASH model mice, 0.05 mL of blood was collected from each mouse on day when it became 8 weeks old by a jugular vein blood collection method. The collected blood was immediately put in a centrifuge tube charged with heparin, was centrifuged at 3000 rpm for 10 minutes to obtain plasma, and an ALT level was measured by using Drychem (Fujifilm Corporation). On the basis of the ALT level, the weight and the blood glucose level, the mice were grouped by stratified randomization assignment using a statistical analysis system EXSUS 7.7 (manufactured by CAC Exicare Corporation) into a group of mice to be administered with a neutralized ume juice concentrate and a control mouse group for the following examination. The weight of each mouse was measured every week after day of grouping, and on day of necropsy.

Dosage Form

From a next day after becoming 8 weeks old, an administration test for a 1.7-fold diluted solution, with distilled water, of the (solution of) heated neutralized ume juice concentrate with insolubles removed prepared in Example 1 (designated as the "neutralized diluted ume juice concentrate") was performed. The mice were raised by allowing the neutralized diluted ume juice concentrate-administered mouse group and the control mouse group to freely eat HFD 32, and the standard mouse group to freely eat CRF-1, and all the groups to freely drink distilled water. Besides, for 28 days continuously after starting the administration, 10 mL/kg (body weight) of the neutralized diluted ume juice concentrate was administered to the neutralized diluted ume juice concentrate-administered mouse group and 10 mL/kg (body weight) of distilled water was administered to the control mouse group by using an oral gastric tube once between 9 and 11 o'clock a.m. and once between 5 and 7 o'clock p.m.

On day of necropsy corresponding to 28 days after starting the administration test for the neutralized diluted ume juice concentrate, the STZ-induced NASH model mice of 12 weeks old were fasted for 2 hours, and blood was collected from abdominal vena cava under anesthesia with Somnopentyl. The thus obtained blood was immediately put in a centrifuge tube charged with heparin, and was centrifuged at 3000 rpm for 10 minutes to obtain plasma. After confirming euthanasia by exsanguination, the liver was collected, and a part of the liver was immersed in buffered formalin.

Sirius Red-Stained Image

From the formalin-immersed liver, paraffin sections were prepared. Hematoxylin staining and Sirius red staining were carried out using Picrosirius Red Stain Kit (Cosmo Bio Co., Ltd.). Images of a section sample having been subjected to the Sirius red staining were taken by using an all-in-one fluorescence microscope (BZ-9000, manufactured by Keyence Corporation) with a 10× objective lens, and thus, a connected image was produced. The results are illustrated in FIGS. 1(a) to 1(c).

Results

Figure 1A:
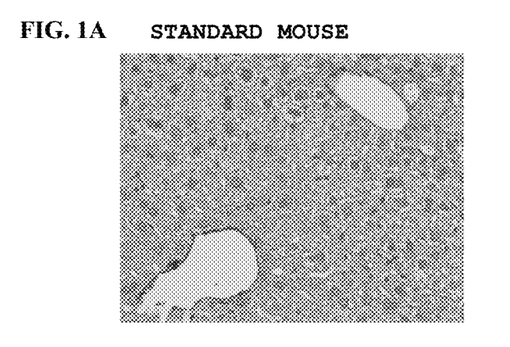
FIG. 1A illustrates liver of a standard mouse.
Figure 1B:
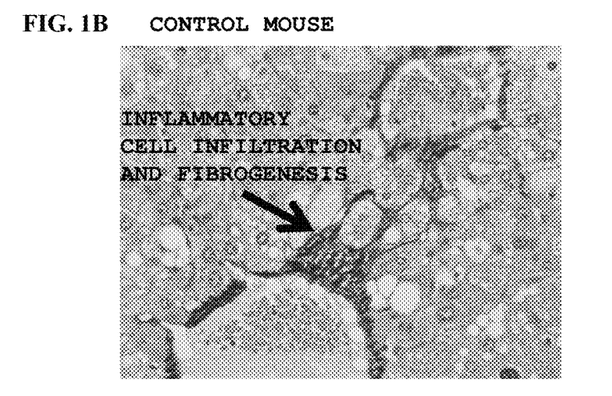
FIG. 1B illustrates liver of an STZ-induced NASH model mouse (a control mouse)
Figure 1C:
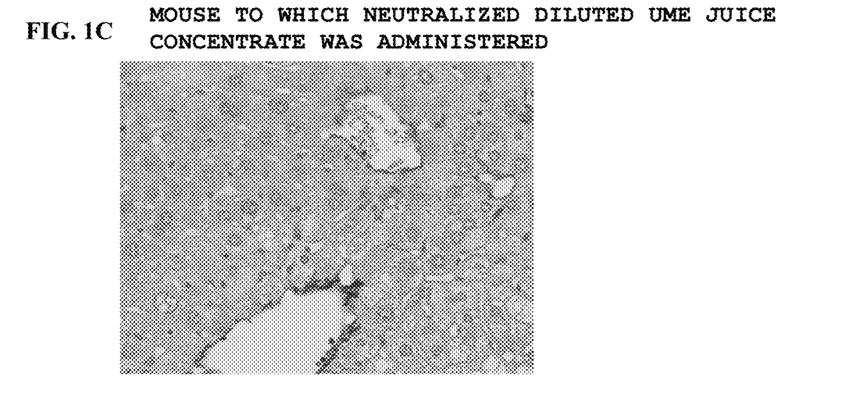
FIG. 1C illustrates liver of an STZ-induced NASH model mouse administered with a neutralized diluted ume juice concentrate.

As is obvious from FIG. 1(a), Sirius red positive collagen fiber was found only in a vascular basement membrane and disease reacted fibrogenesis was not found in the liver of the standard mouse not administered with STZ, but as is obvious from FIG. 1(b), inflammatory cell infiltration and Sirius red positive collagen expanded around liver cells were observed in the image of the liver of the control mouse not administered with the neutralized diluted ume juice concentrate but administered with STZ, and thus, liver fibrogenesis was found (particularly in a portion indicated with an arrow). On the other hand, as is obvious from FIG. 1(c), the inflammatory cell infiltration and the fibrogenesis were not observed in the liver of the mouse administered with the neutralized diluted ume juice concentrate. Accordingly, it was confirmed that the oral administration of the neutralized diluted ume juice concentrate has an effect to eliminate the inflammatory cell infiltration and the fibrogenesis in the liver of the STZ-induced NASH model mouse.

Quantitative Determination of Sirius Red Positive Region

Figure 2:
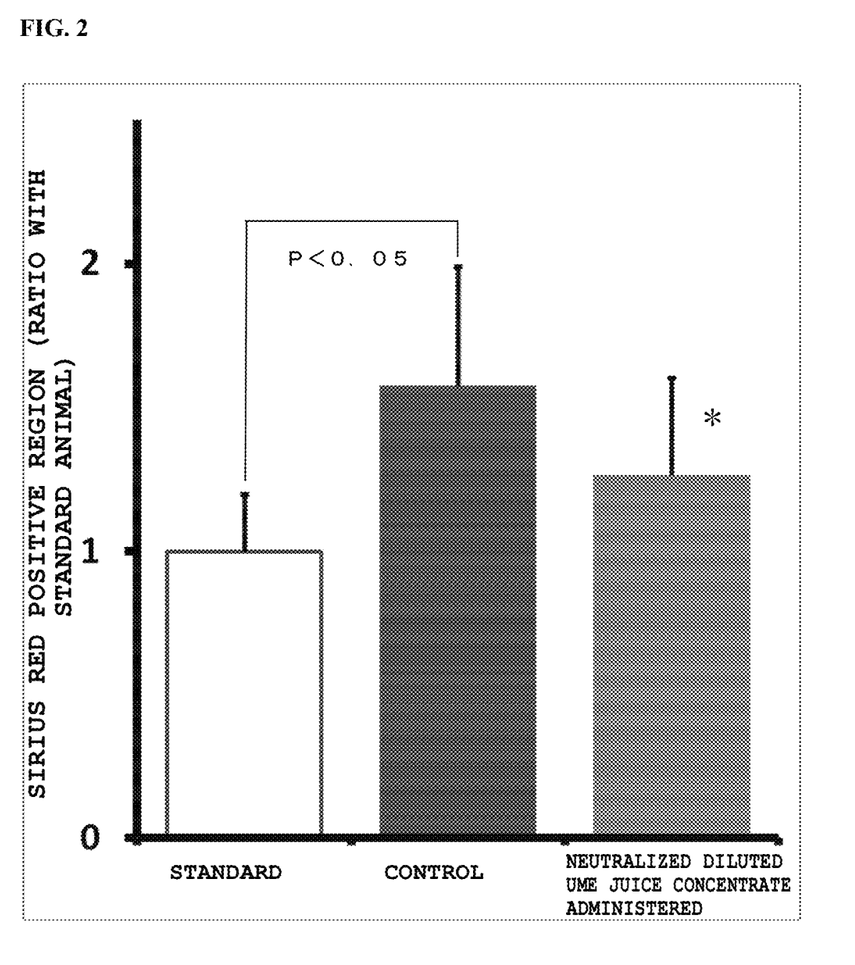
FIG. 2 is a graph illustrating quantitative determination of a Sirius red positive region in a 12-week-old standard mouse, a 12-week-old STZ-induced NASH model mouse, and a 12-week-old STZ-induced NASH model mouse on day 28 after starting an administration test for a neutralized diluted ume juice concentrate.

In the connected image, an area of a Sirius red positive region was extracted by using BZ-II image analysis application, and assuming that the area of the standard mice (n=7) was 1, ratios of the control mice (n=18) and the neutralized diluted ume juice concentrate-administered mice (n=18) were calculated and plotted in a graph of FIG. 2. It was determined by a significance test (Student's t test) that there was a significant difference when p<0.05.

Results

As is obvious from FIG. 2, assuming that the area of the standard mouse (n=7) was 1, the value of the Sirius red positive region of the control mouse was 1.55, the value of the Sirius red positive region of the neutralized diluted ume juice concentrate-administered mouse was 1.26, and thus, the value was significantly reduced (* shown in the drawing indicates that a P value was found to be 0.05 or less in the significance test for the comparison between the STZ-administered control mouse group and the neutralized diluted ume juice concentrate-administered mouse group). It was thus confirmed that the oral administration of the neutralized diluted ume juice concentrate has an effect to prevent and/or treat the inflammatory cell infiltration and the fibrogenesis in the liver of the NASH model mouse.

Plasma Albumin Level

It is known that there is correlation between a plasma albumin concentration and a cumulative survival rate of a decompensated liver cirrhosis patient, and that the prognosis is better when the plasma albumin concentration is high, and therefore, an albumin concentration in plasma was measured in the three types of mice. The results are illustrated in FIG. 3.

Results

Figure 3:
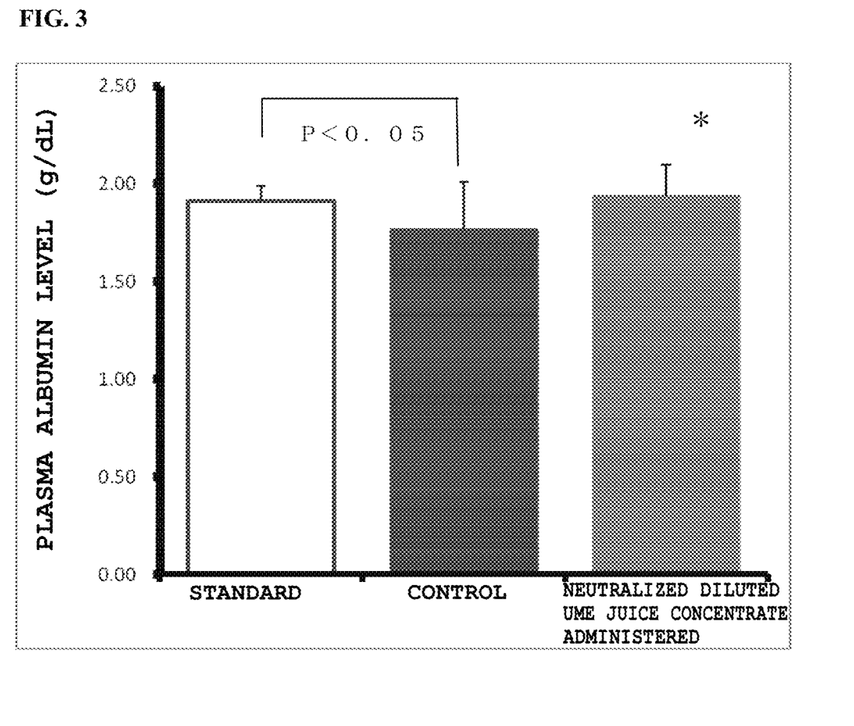
FIG. 3 is a graph illustrating plasma albumin levels of a standard mouse, an STZ-induced NASH model mouse, and an STZ-induced NASH model mouse administered with a neutralized diluted ume juice concentrate.

As is obvious from FIG. 3, the plasma albumin concentration of the standard mouse was 1.91 g/dL, and the plasma albumin concentration of the control mouse was 1.77 g/dL. On the other hand, the plasma albumin concentration of the neutralized diluted ume juice concentrate-administered mouse was 1.96 g/dL, and thus, it was confirmed that the oral administration of the neutralized diluted ume juice concentrate has possibility of increasing the plasma albumin level and increasing the survival rate (* shown in the drawing indicates that a P value was found to be 0.05 or less in a significance test performed by Student's t test for the comparison between the STZ-administered control mouse group and the neutralized diluted ume juice concentrate-administered mouse group).

Plasma Total Protein Level

It is known that when the liver function is deteriorated through progression of the liver disease, the protein synthesis ability of the liver is lowered (Hepatology 1984 May-June; 4(3): 430-5), and therefore, a plasma total protein level was measured in the three types of mice. The results are illustrated in FIG. 4.

Results

Figure 4:
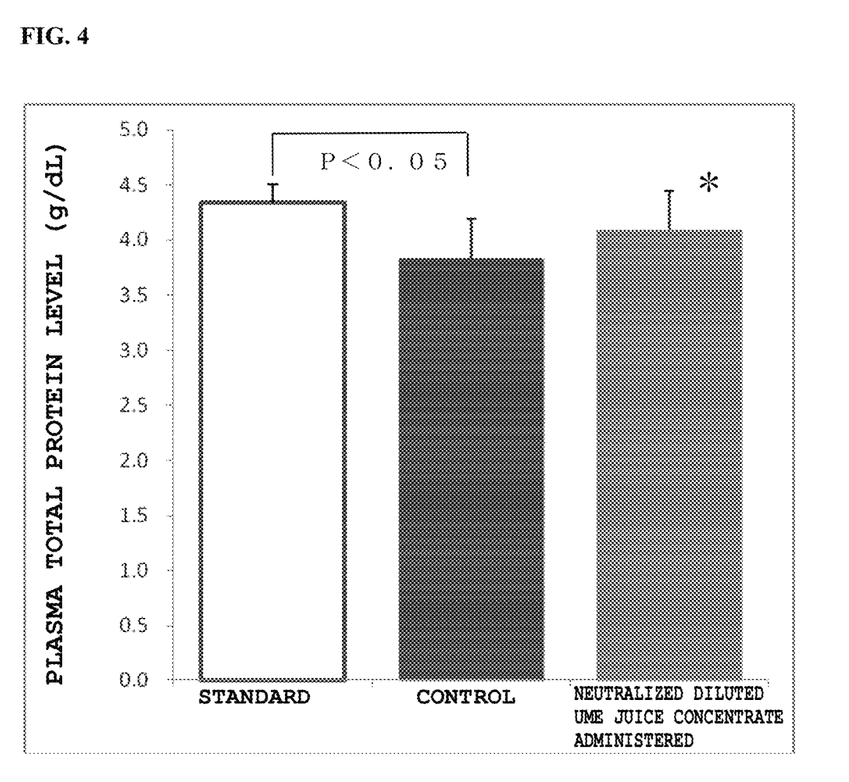
FIG. 4 is a graph illustrating plasma total protein levels of a standard mouse, an STZ-induced NASH model mouse, and an STZ-induced NASH model mouse administered with a neutralized diluted ume juice concentrate.

As is obvious from FIG. 4, the plasma total protein level of the standard mouse was 4.34 g/dL, and the plasma total protein level of the control mouse was 3.83 g/dL. On the other hand, the plasma total protein level of the neutralized diluted ume juice concentrate-administered mouse was 4.10 g/dL, and thus, it was confirmed that the oral administration of the neutralized diluted ume juice concentrate has possibilities of increasing the plasma total protein level and increasing the protein synthesis ability in the liver (* shown in the drawing indicates that a P value was found to be 0.05 or less in the significance test performed by Student's t test for the comparison between the STZ-administered control mouse group and the neutralized diluted ume juice concentrate-administered mouse group).

Liver Function Index

An aspartate transaminase (AST) concentration and an alanine transaminase (ALT) concentration in plasma of the three types of mice were measured using Fuji Drychem biochemical analyzer. The results are illustrated in FIGS. 5(a) to 5(c) together with the weight of mice used in the experiment.

Results

Figure 5A:
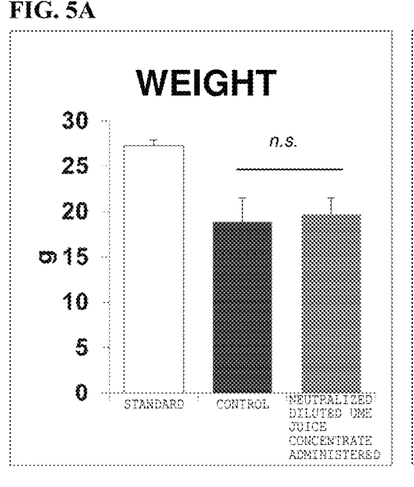
FIGS. 5A, 5B and 5C illustrate graphs of weights (FIG. 5A), ALT levels (FIG. 5B), and AST levels (FIG. 5C) of a standard mouse, an STZ-induced NASH model mouse, and an STZ-induced NASH model mouse administered with a neutralized diluted ume juice concentrate.
Figure 5B:
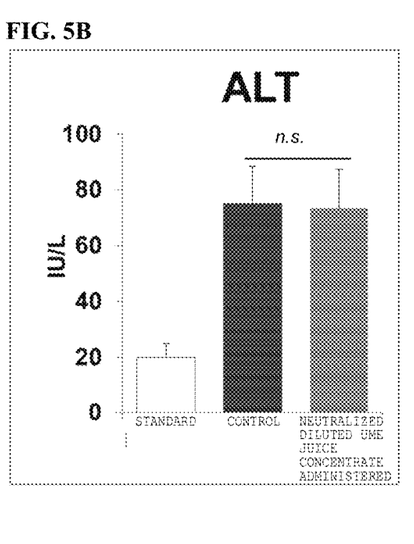
Figure 5C:
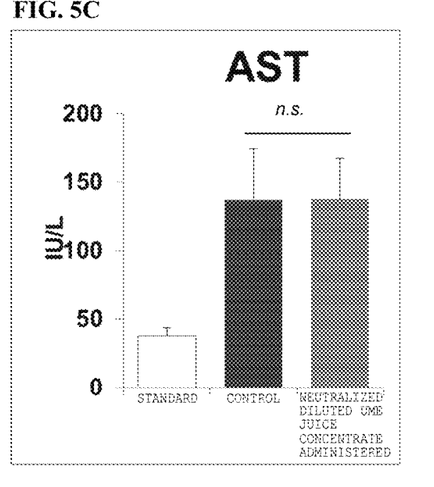

As is obvious from FIG. 5(a), the weight was reduced in the control mice and the neutralized diluted ume juice concentrate-administered mice as compared with that of the standard mice. The ALT level and the AST level were higher in the control mouse and the neutralized diluted ume juice concentrate-administered mice as compared with the standard mice (n.s. in the drawing indicates that a P value was found to be larger than 0.05 in a significance test performed by Student's t test for the comparison between the STZ-administered control mouse group and the neutralized diluted ume juice concentrate-administered mouse group).

Conclusion

When the neutralized diluted ume juice concentrate was orally administered to the STZ-induced NASH model mice of 8 to 12 weeks old, it was confirmed that there is no difference in the AST and ALT levels but the fibrogenesis was significantly reduced, and thus, it was found that the neutralized diluted ume juice concentrate has an effect to reduce the fibrogenesis in NASH. Besides, it was confirmed that the progression to liver fibrosis can be suppressed even when the mouse was 12 weeks old. Furthermore, it was confirmed that the plasma albumin level/total protein level are significantly increased by the administration of the neutralized diluted ume juice concentrate, and thus the liver function was improved.

Example 4

Preparation of STZ-Induced NAFLD Model Mouse

To the STZ-induced NAFLD model mice that had become 5 weeks old, the neutralized diluted ume juice concentrate was administered from next day after becoming 5 weeks old.

On day of necropsy corresponding to 21 days after starting the administration test for the neutralized diluted ume juice concentrate, the STZ-induced NAFLD model mice of 8 weeks old were fasted for 2 hours, and blood was collected from abdominal vena cava under anesthesia with Somnopentyl. The thus obtained blood was immediately put in a centrifuge tube charged with heparin, and was centrifuged at 3000 rpm for 10 minutes to obtain plasma. After confirming euthanasia by exsanguination, the liver was collected, and a part of the liver was immersed in buffered formalin.

Sirius Red-Stained Image

From the formalin-immersed liver, paraffin sections were prepared. Hematoxylin staining and Sirius red staining were carried out using Picrosirius Red Stain Kit. Images of a section sample having been subjected to the Sirius red staining were taken by using an all-in-one fluorescence microscope with a 10× objective lens, and thus, a connected image was produced. The results are illustrated in FIGS. 6(a) and 6(b).

Results

Figure 6A:
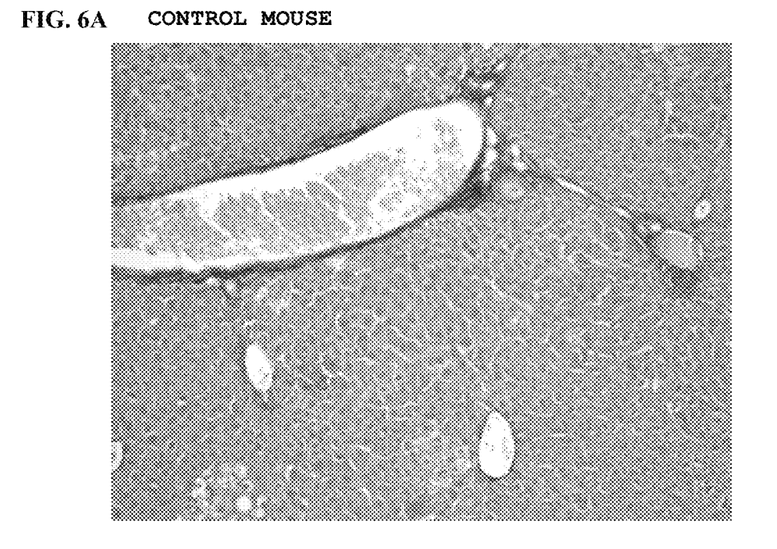
FIG. 6A illustrates liver of an STZ-induced NAFLD model mouse (a control mouse)
Figure 6B:
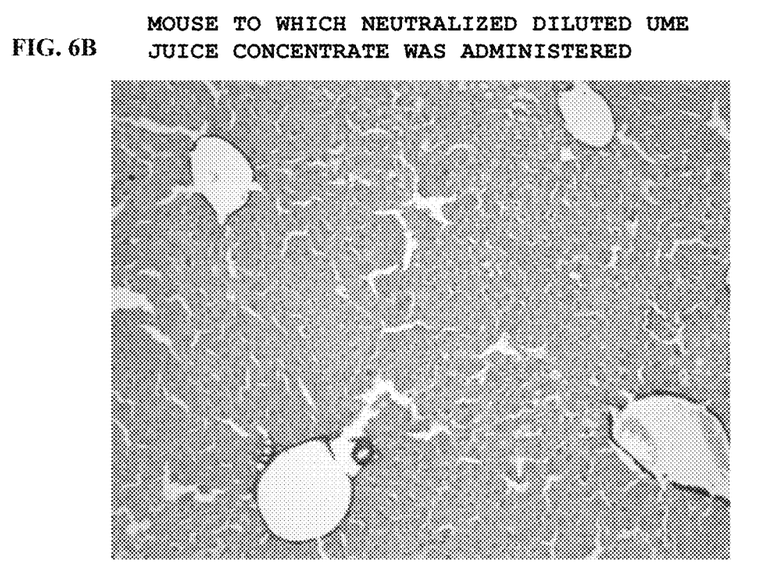
FIG. 6B illustrates liver of an STZ-induced NAFLD model mouse administered with a neutralized diluted ume juice concentrate.

As is obvious from FIG. 6(a), in the liver of the control NAFLD model mouse not administered with the neutralized diluted ume juice concentrate but administered with STZ, the accumulation of inflammatory cells around blood vessels, the deposition of fat in liver cells, and expansion of a Sirius red positive collagen fibrogenesis region were found, and thus, the progression to NASH was confirmed. On the other hand, as is obvious from FIG. 6(b), in the liver of the mouse administered with the neutralized diluted ume juice concentrate, the inflammatory cell infiltration, the fat deposition in liver cells and the expanded fibrogenesis around blood vessels were not substantially found. Accordingly, it was confirmed that the oral administration of the neutralized diluted ume juice concentrate has an effect to suppress the inflammatory cell infiltration and the fibrogenesis in the liver of the STZ-induced NAFLD model mouse, and has an effect to improve or treat NAFLD and to prevent NASH.

Quantitative Determination of Sirius Red Positive Region

Figure 7:
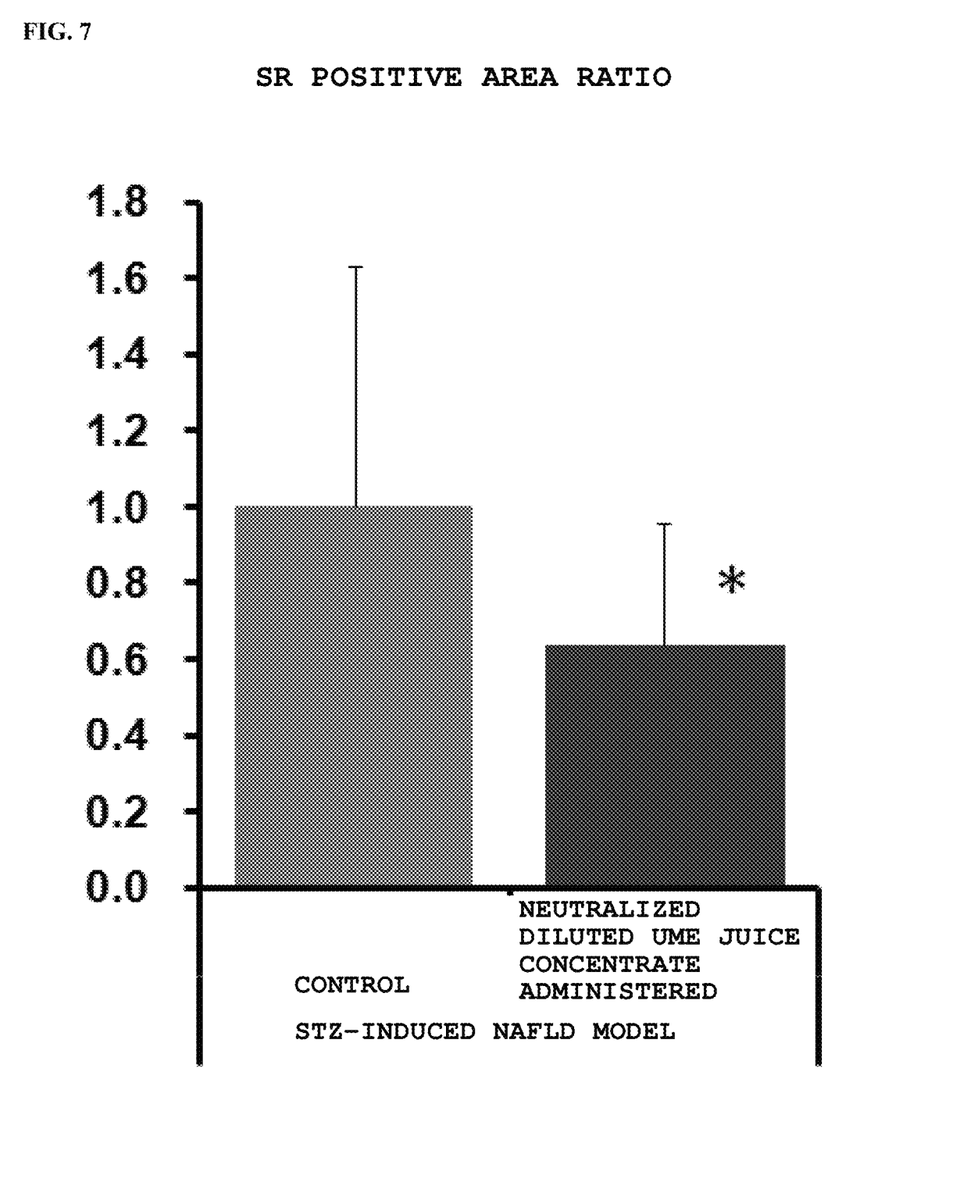
FIG. 7 is a graph illustrating quantitative determination of a Sirius red positive region in an 8-week-old STZ-induced NAFLD model mouse and an 8-week-old STZ-induced NAFLD model mouse on day 21 after starting an administration test for a neutralized diluted ume juice concentrate.

In the connected image, an area of a Sirius red positive region was extracted by using BZ-II image analysis application, and assuming that the area of control mice (n=19) was 1, a ratio of the neutralized diluted ume juice concentrate-administered mice (n=19) was calculated and plotted in a graph of FIG. 7. It was determined by a significance test (Student's t test) that there was a significant difference when $p<0.05$.

Results

As is obvious from FIG. 7, assuming that the area of the control mice (n=19) was 1, the value of the Sirius red positive region of the neutralized diluted ume juice concentrate-administered mice (n=19) was 0.63, and thus, the value was significantly reduced (* shown in the drawing indicates that it was determined by the significance test that there was a significant difference between the STZ-administered control mouse group and the neutralized diluted ume juice concentrate-administered mouse group).

Liver Function Index

The AST level and the ALT level in plasma of the three types of mice of standard mice (n=7), control mice (n=19) and neutralized diluted ume juice concentrate-administered mice (n=19) were measured by JSCC standardization corresponding method using Hitachi 7180 automatic analyzer. The results are illustrated in FIGS. 8(a) and 8(b).

Results

Figure 8A:
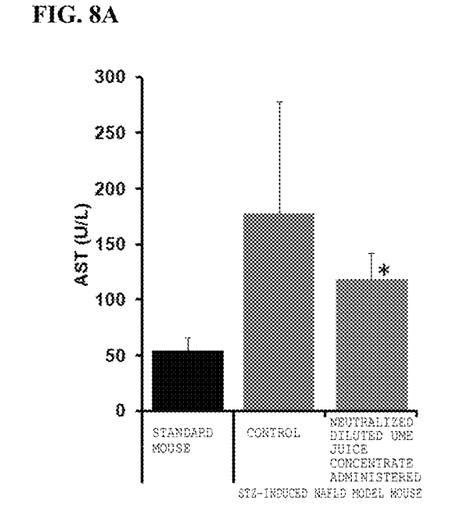
FIGS. 8A and 8B illustrate graphs of AST levels (FIG. 8(a)), and ALT levels (FIG. 8(b)) of an STZ-induced NAFLD model mouse and an STZ-induced NAFLD model mouse administered with a neutralized diluted ume juice concentrate.
Figure 8B:
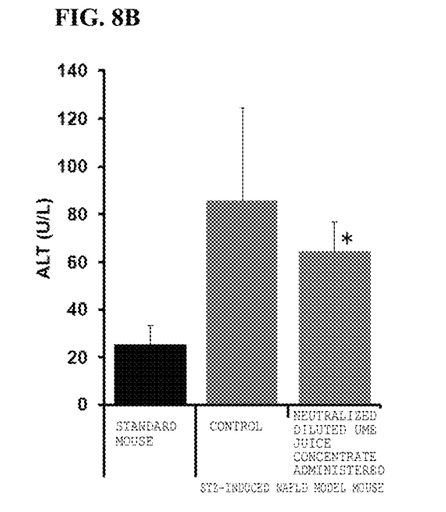

As is obvious from FIGS. 8(a) and 8(b), the AST level and the ALT level were significantly lower in the neutralized diluted ume juice concentrate-administered mouse as compared with the control mouse (* shown in the drawing indicates that a P value was found to be 0.05 or less in the significance test performed by Student's t test for the comparison between the control mouse group and the neutralized diluted ume juice concentrate-administered mouse group).

Hematoxylin/Eosin Staining

The paraffin sections prepared from control mice and neutralized diluted ume juice concentrate-administered mice were used for hematoxylin/eosin staining. Sections prepared from individuals having AST and ALT levels close to averages of the AST and ALT levels of these groups were selected, and results obtained by observation of pathological images with an all-in-one fluorescence microscope (BZ-9000, manufactured by Keyence Corporation) with a 4× objective lens are illustrated in FIGS. 9(a) and 9(b).

Figure 9A:
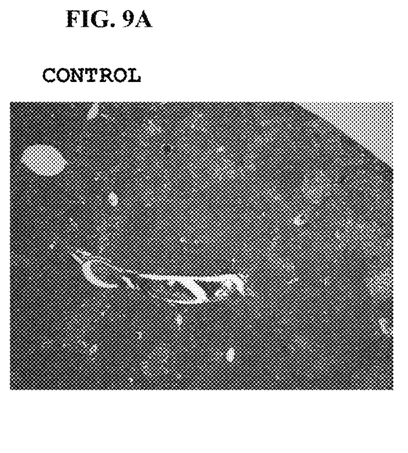
FIG. 9A illustrates liver of a control STZ-induced NAFLD model mouse.
Figure 9B:
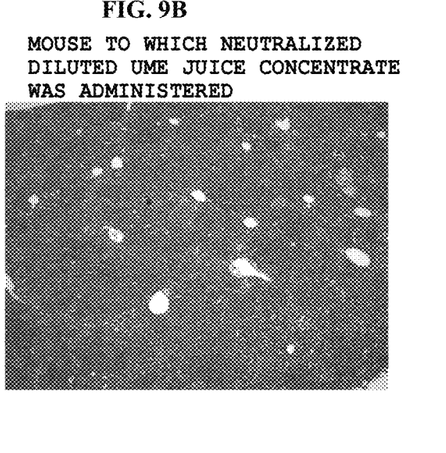
FIG. 9B illustrates liver of an STZ-induced NAFLD model mouse administered with a neutralized diluted ume juice concentrate.

As is obvious from FIGS. 9(a) and 9(b), a large number of small fat droplets were deposited in the control mouse of FIG. 9(a). No fat droplets were found in the neutralized diluted ume juice concentrate-administered mouse of FIG. 9(b).

Conclusion

When the neutralized diluted ume juice concentrate was orally administered to an STZ-induced NAFLD model mouse of 5 to 8 weeks old, it was confirmed that the AST and ALT levels are significantly lowered, that fat deposition is significantly reduced, and that an effect to suppress occurrence of the fibrogenesis is obtained. Accordingly, it was confirmed that the inflammatory cell infiltration can be prevented in the liver of the NAFLD model mouse to suppress the progression to NASH even when the mouse is 8 weeks old.

Overview

The ume juice concentrate or the processed product thereof of the present invention is useful in the medical field from the viewpoint that NAFLD or NASH can be prevented and/or treated.

Example 5

Administration of Unneutralized Solution of Heated Ume Juice Concentrate

Materials and Method

An 8-week old Wistar male rat was used as an animal. The heated ume juice concentrate of Example 1 was diluted with water of a substantially equivalent weight to obtain a solution of the heated ume juice concentrate, and the resultant was further diluted with water to obtain an unneutralized solution (37 w/v % solution) of the heated ume juice concentrate. An administration solution obtained by diluting this unneutralized solution of the heated ume juice concentrate to the same concentration employed in the test of Example 3 (a diluted solution of the unneutralized heated ume juice concentrate) was orally administered to the animal at a dose of 6 g/kg for 8 days to be compared with a case where the same amount of distilled water was administered (control group). After administering the test substance on day 7 after starting the administration, D(+)-galactosamine hydrochloride was intraperitoneally administered at a dose of 750 mg/2.5 mL/kg to induce acute liver injury. Forty-eight (48) hours after the administration of the galactosamine, exsanguination was caused through the abdominal aorta under anesthesia with pentobarbital, and the liver was collected to be fixed with formalin and subjected to the hematoxylin/eosin staining. Besides, it was confirmed that cells appearing in the hepatic lobule of the galactosamine-administered rats were activated stellate cells positive for immunostaining (Histofine Staining Kit of Nichirei Corporation) using an anti-α smooth muscle actin antibody (Proteintech).

Results

Figure 10A:
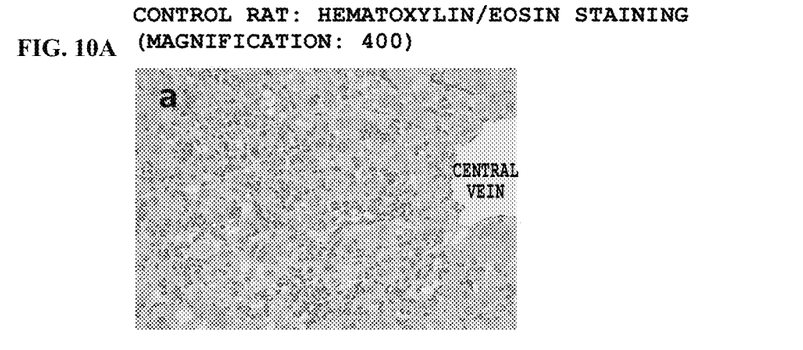
FIG. 10A is a micrograph (magnification: 400) of liver tissue of a control rat administered with distilled water having been subjected to hematoxylin/eosin staining.
Figure 10B:
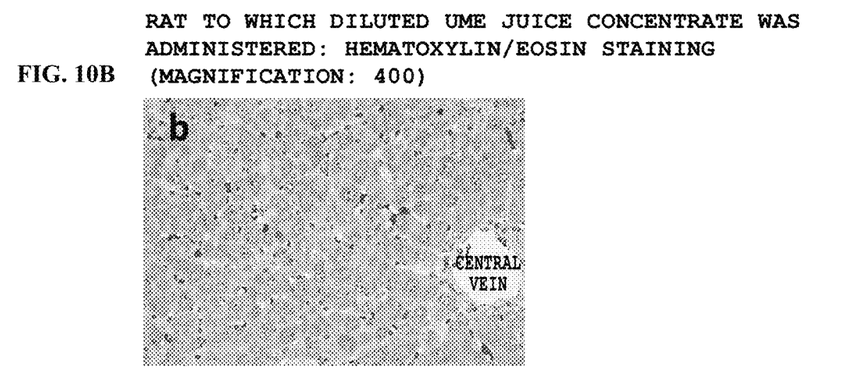
FIG. 10B is a micrograph (magnification: 400) of liver tissue of a rat administered with an unneutralized diluted solution of a heated ume juice concentrate.
Figure 10C:
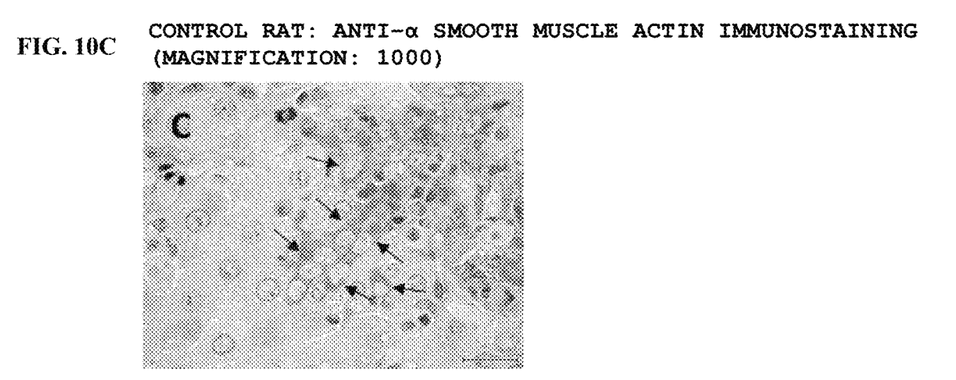
FIG. 10C is a micrograph (magnification: 1000) of liver tissue of a control rat having been subjected to immunostaining with an anti-α smooth muscle actin antibody.

With respect to liver tissue, while an accumulation pattern of small fiber producing cells was found in the hepatic lobule in the group administered with distilled water (FIG. 10(a)), the accumulation of such fiber producing cells was remarkably reduced in the group administered with the administration solution of the ume juice concentrate (FIG. 10(b)). The small fiber producing cells accumulated in the hepatic lobule of the control group are activated stellate cells positive for the anti-α smooth muscle actin antibody and are cells responsible for the fibrogenesis in the liver tissue. It was found, based on these results, that the appearance of the activated stellate cells responsible for the fibrogenesis in the liver accompanied by the liver injury induced by the administration of galactosamine was suppressed in the group administered with the administration solution of the ume juice concentrate. FIG. 10(c) illustrates that the cells appearing in the hepatic lobule through the galactosamine administration are activated stellate cells (cells indicated with arrows) positive for the immunostaining with the anti-α smooth muscle actin antibody.

INDUSTRIAL APPLICABILITY

An ume juice concentrate or a processed product thereof of the present invention is extremely useful in the medical field from the viewpoint that NAFLD or NASH can be prevented and/or treated.

The invention claimed is:

1. A method for treating or lowering the incidence or progression of non-alcohol steatohepatitis (NASH), comprising administering an effective amount of an ume juice concentrate or a processed product thereof to a subject in need of reduction of fibrogenesis in liver tissue.

2. The method according to claim 1, wherein the processed product of the concentrate is a neutralized processed product of the concentrate.

3. The method according to claim 1, wherein the concentrate is a heated concentrate.

4. The method according to claim 1, wherein the ume juice concentrate or the processed product thereof is administered orally.

5. The method according to claim 1, wherein the ume juice concentrate or the processed product thereof is used as a dietary supplement.

6. The method according to claim 2, wherein the concentrate is a heated concentrate.

7. The method according to claim 2, wherein the ume juice concentrate or the processed product thereof is administered orally.

8. The method according to claim 3, wherein the ume juice concentrate or the processed product thereof is administered orally.

9. The method according to claim 6, wherein the ume juice concentrate or the processed product thereof is administered orally.

* * * * *